(12) United States Patent
Tsuruta et al.

(10) Patent No.: US 10,234,367 B2
(45) Date of Patent: Mar. 19, 2019

(54) HYDRAULIC TEST METHOD AND HYDRAULIC TEST DEVICE

(71) Applicant: NAKATA MANUFACTURING CO., LTD., Osaka (JP)

(72) Inventors: Satoshi Tsuruta, Osaka (JP); Katsuhiko Morisaki, Osaka (JP); Mitsuru Nakata, Osaka (JP); Katsumi Ishigaki, Osaka (JP)

(73) Assignee: NAKATA MANUFACTURING CO., LTD., Osaka (JP)

( * ) Notice: Subject to any disclaimer, the term of this patent is extended or adjusted under 35 U.S.C. 154(b) by 252 days.

(21) Appl. No.: 15/115,729

(22) PCT Filed: Feb. 4, 2014

(86) PCT No.: PCT/JP2014/052575
§ 371 (c)(1),
(2) Date: Aug. 1, 2016

(87) PCT Pub. No.: WO2015/118614
PCT Pub. Date: Aug. 13, 2015

(65) Prior Publication Data
US 2017/0167961 A1 Jun. 15, 2017

(51) Int. Cl.
*G01N 3/12* (2006.01)
*G01M 3/28* (2006.01)
*G01M 5/00* (2006.01)

(52) U.S. Cl.
CPC ............ *G01N 3/12* (2013.01); *G01M 3/2846* (2013.01); *G01M 5/0058* (2013.01);
(Continued)

(58) Field of Classification Search
CPC ............ G01N 3/12; G01N 2203/0274; G01N 2203/0208; G01N 2203/0003; G01N 2203/0048; G01M 3/2846
See application file for complete search history.

(56) References Cited

U.S. PATENT DOCUMENTS 3,312,103 A * 4/1967 Goeke .................... F15B 11/02
137/115.16
4,416,147 A * 11/1983 Hasha ................. G01M 3/2846
73/49.4
(Continued)

FOREIGN PATENT DOCUMENTS

CN 101709725 A 5/2010
CN 102042935 A 5/2011
(Continued)

OTHER PUBLICATIONS

International Preliminary Report on Patentability issued in PCT/JP2014/052575; dated Aug. 9, 2016.
(Continued)

*Primary Examiner* — Xin Y Zhong
(74) *Attorney, Agent, or Firm* — Studebaker & Brackett PC

(57) ABSTRACT

A water hydraulic test on test pipes having a wide range of sizes is conducted accurately, efficiently, and economically, by using a plurality of booster cylinders arranged in parallel with respect to a test pipe and having respective boosting ratios increasing in stages. A plurality of servo motor driven pumps arranged in parallel is used as a drive source for the plurality of booster cylinders. Before a water pressure on an output side of the booster cylinder reaches a pressure near a test pressure, the plurality of servo motor driven pumps operates simultaneously. Then, the plurality of servo motor driven pumps stops operating except one and the water pressure on the output side of the booster cylinder is increased to the test pressure by the one servo motor driven pump. During pressure increase, the plurality of booster cylinders is used in turn in order of increasing boosting ratio.

8 Claims, 7 Drawing Sheets

(52) U.S. Cl.
CPC ............. *G01N 2203/0003* (2013.01); *G01N 2203/0048* (2013.01); *G01N 2203/0208* (2013.01); *G01N 2203/0274* (2013.01)

(56) References Cited

U.S. PATENT DOCUMENTS

| | | | |
|---|---|---|---|
| 4,770,019 A | | 9/1988 | Kuramoto et al. |
| 5,152,167 A | * | 10/1992 | Moody ............... G01M 3/3236 73/40 |
| 2007/0143049 A1 | | 6/2007 | Thomalla et al. |

FOREIGN PATENT DOCUMENTS

| | | |
|---|---|---|
| JP | S55-075634 A | 6/1980 |
| JP | S5575634 A | 6/1980 |
| JP | S63-115902 A | 5/1988 |
| JP | S63115902 A | 5/1988 |
| JP | H02-268247 A | 11/1990 |
| JP | H02268247 A | 11/1990 |
| JP | H04-362285 A | 12/1992 |
| JP | H04362285 A | 12/1992 |
| JP | H07-286948 A | 10/1995 |
| JP | H07286948 A | 10/1995 |
| JP | H08-187155 A | 7/1996 |
| JP | H08187755 A | 7/1996 |
| JP | 3137530 B2 | 2/2001 |
| JP | 2007-509329 A | 4/2007 |
| JP | 4738783 B2 | 8/2011 |
| JP | 5783656 B1 | 9/2015 |
| WO | 2013/005283 A1 | 1/2013 |

OTHER PUBLICATIONS

Written Opinion issued in PCT/JP2014/052575; dated Apr. 8, 2014.
International Search Report issued in PCT/JP2014/052575; dated Apr. 8, 2014.

* cited by examiner

Prior Art

Prior Art

Prior Art

Prior Art

HYDRAULIC TEST METHOD AND HYDRAULIC TEST DEVICE

TECHNICAL FIELD

This invention relates to a water hydraulic test method implemented to examine the quality of a welded pipe such as an electric resistance welded pipe or a spiral pipe and a seamless pipe. More specifically, this invention relates to a water hydraulic test method and a water hydraulic test device by which the inside of a test pipe is pressurized to a predetermined pressure and held at the predetermined pressure by filling the test pipe with water entirely and then pouring high-pressure water into the test pipe using an oil hydraulically driven booster cylinder.

BACKGROUND ART

In a manufacturing line of an electric resistance welded pipe, a water hydraulic test is conducted to examine the quality of the manufactured electric resistance welded pipe, particularly the quality of a welded part called a seam part. This water hydraulic test is conducted by putting the manufactured electric resistance welded pipe of a given length between a headstock and a tailstock arranged at the front and the back of a test line, hermetically sealing the pipe at both of the front and back ends thereof, and pouring high-pressure water into the electric resistance welded pipe in this state through the headstock. The pressure of the high-pressure water reaches about 90% of assured strength. An electric resistance welded pipe having withstood this pressure for a predetermined time and not causing breakage of a welded part and not causing resultant burst of the pipe is determined to be a conforming item in terms of mechanical strength.

The following describes the outline of a procedure of the water hydraulic test. A test pipe is fixed between a headstock and a tailstock and hermetically sealed at both of opposite ends thereof. Water is poured at a low pressure (including the self weight of the water) into the test pipe from a tank through the headstock. Air in the test pipe is exhausted to the outside of the pipe through the tailstock. When the test pipe is substantially full of water, high-pressure water is supplied forcibly into the test pipe to pressurize the inside of the pipe to a required test pressure. The inside of the pipe is held at the test pressure for a predetermined time and then the pressure test is finished. After the pressure test is finished, a pressure reducing valve provided on a tail side, on a head side, or each of the tail side and the head side is opened to reduce the pressure in the pipe. Then, the test pipe is removed from between the both stocks and water in the pipe is discharged to a pit. In this way, the test is finished completely.

As described in patent literature 1, a booster mechanism using oil pressure is employed as a high-pressure water supply system of supplying high-pressure water forcibly into a test pipe. Specifically, high-pressure water is supplied into the test pipe using an oil hydraulically driven booster cylinder. More specifically, water is sucked into an output side of the oil hydraulically driven booster cylinder and then pressure oil is supplied to increase a pressure on an input side of the cylinder. This makes a piston in the cylinder advance to supply high-pressure water from the output side of the booster cylinder into the headstock and eventually, into the test pipe.

As shown in FIG. 4, a plurality of oil hydraulic pumps 1 arranged in parallel is used simultaneously as a drive system for the booster cylinder, specifically, as an oil hydraulic source from which pressure oil is supplied to the input side of the booster cylinder. The reason therefor is that, as the water pressure, the water quantity, and the supply pattern of high-pressure water to be supplied to a test pipe change in various ways in a manner that depends on the size of the test pipe, etc., the oil pressure and the oil quantity of pressure oil to be supplied to the input side of the booster cylinder are also required to cover a wide range.

Oil hydraulic control is executed using a proportional control valve 4 placed as a check valve in a secondary line 3 branching from a main line 2 extending from the plurality of oil hydraulic pumps 1 to an input side of a booster cylinder 5. Like the reason of simultaneously using the plurality of oil hydraulic pumps 1 arranged in parallel, reason of placing the oil hydraulic control valve not in the main line 2 but in the secondary line 3 branching from the main line 2 is that pressure oil to be supplied to the booster cylinder 5 is required to cover a wide range from a low pressure and a low flow rate to a high pressure and a high flow rate.

The plurality of oil hydraulic pumps 1 is a generally-used oil hydraulic unit driven by an AC motor. Thus, the oil hydraulic pumps 1 continue discharging pressure oil by rotating constantly. The pressure of the discharged pressure oil is controlled using the proportional control valve placed as a check valve in the secondary line. Specifically, if the pressure of pressure oil in the main line 2 is higher than a set pressure at the proportional control valve 4 in the secondary line 3, pressure oil is released through the proportional control valve 4 so as to maintain the set pressure. In this way, the pressure of the pressure oil in the main line 2 is maintained at the set pressure. As shown in FIG. 5, the oil pressure and the oil quantity of the oil hydraulic pump 1 are in inverse proportion to each other. The oil pressure and the pressure of high-pressure water are in proportion to each other. The oil pressure and the quantity of the high-pressure water are in proportion to each other.

In an actual water hydraulic test, a set oil pressure at the proportional control valve 4 is increased in stages such as 10 MPa, 20 MPa, and 30 MPa, for example, to shift to a set hold-on pressure finally. In response, as shown in FIG. 6, the pressure of high-pressure water is increased in stages to finally reach a hold-on pressure. The flow rate of the high-pressure water is reduced with increase in a pressure. While the hold-on pressure is maintained, this flow rate is substantially zero. At this time, in the drive system for the booster cylinder 5, much of pressure oil discharged from the plurality of oil hydraulic pumps 1 is released to the outside of the line through the proportional control valve 4 in the secondary line 3.

The following describes why the flow rate of high-pressure water to be supplied into a test pipe is reduced while the pressure of the high-pressure water is increased in stages. If a pressure at the proportional control valve 4 is set a maximum pressure corresponding to the hold-on pressure from the beginning, a pressure on the input side of the booster cylinder is increased while a high flow rate is maintained. As a result, an overshoot is caused in the pressure of the high-pressure water by the inertial force of the booster cylinder itself (inertial force of a piston), etc., to make the pressure of the high-pressure water exceed its upper limit, as shown in FIG. 7.

The hold-on pressure of the high-pressure water is set at a pressure between a pressure required for a test and an upper limit pressure. To prevent the occurrence of an overshoot in the pressure of the high-pressure water, the flow rate of the high-pressure water to be supplied into a test pipe is reduced while the pressure of the high-pressure water is increased in stages. Further, in an attempt to absorb the aforementioned inertial force completely, the set pressure at the proportional control valve is adjusted to a final pressure corresponding to the hold-on pressure immediately before the pressure of the high-pressure water reaches its hold-on pressure.

The aforementioned high-pressure water supply system using the booster cylinder and the aforementioned drive system for the booster cylinder, high-pressure water at a required pressure can be held for a required time in a test pipe. Meanwhile, increasing a pressure in the test pipe in stages to the required pressure increases what is called a cycle time. This causes an essential problem in that the number of pipes processed per unit time is increased to result in low efficiency. Additionally, an oil hydraulic pump continues rotating constantly, both in a period of increasing the pressure of the booster cylinder and in a period of not increasing the pressure of the booster cylinder. This also causes a problem in that power loss is essentially large in the pump.

Additionally, according to a trend resulting from a breakthrough technique enabling shared use of a shaping roll (patent literature 2) suggested recently, in manufacture of electric resistance welded pipes, electric resistance welded pipes that can be manufactured on one line are allowed to be increased considerably in size (pipe diameter, thickness, or length) from 8-inch diameter to 24-inch diameter or more, for example. In a water hydraulic test on manufactured electric resistance welded pipes, however, this trend causes a difference in the pressure and the quantity of high-pressure water to be poured into test pipes: a water pressure for a test pipe is several times higher than that for another test pipe and a water quantity for a test pipe is as much as 20 times larger than that for another test pipe. This in turn becomes a factor of various problems.

First, a pressure increasing speed and a change point of the pressure increasing speed are set for each difference in the size of a test pipe and each difference in a hold-on pressure. Hence, a huge volume of data should be retained to involve considerably burdensome operation for the setting. Thus, in view of increasing types in recent years manufactured on one line, conducting a water hydraulic test using one test device is considered not to be a realistic way. This causes irrationality in that many water hydraulic test devices are required for one line.

Second, as a result of a wide range of test pipe sizes, if a water hydraulic test is to be conducted using one test device, an oil hydraulic pump should conform to a maximum size. As described above, the oil hydraulic pump always continues discharging pressure oil by rotating constantly. Thus, if a test pipe size is reduced, more pressure oil is released. This causes large power loss in the oil hydraulic pump in a test period as well as in a period when the test is not conducted. Third, making the oil hydraulic pump conform to the maximum size reduces accuracy of controlling an oil pressure and an oil quantity when the oil hydraulic pump is used in a smaller size. These problems also make it difficult to conduct a water hydraulic test using one test device.

During supply of low-pressure water into a test pipe preceding supply of high-pressure water into the test pipe, air inevitably remains in the test pipe. With the air remaining in the test pipe during the supply of low-pressure water, after the supply of high-pressure water into the test pipe is started, the pressure of the high-pressure water is absorbed by compression of the air. Hence, a considerable delay is caused in pressure increase in an initial stage of water supply. This extends a time (cycle time) further required for a test. Additionally, while the air remains in an amount of about 1.5% on average, since the amount of the remaining air varies widely, this causes serious uncertainty. Thus, the remaining of the air also leads to more complicated setting operation.

PRIOR ART LITERATURE

Patent Literature

Patent Literature 1: Japanese Patent No. 4738783
Patent Literature 2: U.S. Pat. No. 4,770,019

SUMMARY OF INVENTION

Problem to be Solved by Invention

It is an object of this invention to provide a water hydraulic test method and a water hydraulic test device by which, even if test pipes have a wide range of sizes, a water hydraulic test on each of the test pipes can be conducted accurately, efficiently, and economically.

Means of Solving Problem

Placing an oil hydraulic control valve directly in a main line extending from an oil hydraulic source such as an oil hydraulic pump to a low-pressure side of a booster cylinder is an effective way for accurate oil hydraulic control on the booster cylinder. However, this way is difficult to follow in the water hydraulic test device for which this invention is intended as pressure oil at a high pressure passes through the main line in large quantity. Hence, a proportional control valve is conventionally placed in a secondary line branching from the main line. However, as described above, this causes various problems including the magnitude of power loss.

With the intention of solving the various conventional problems while maintaining the basic principle of removing an oil hydraulic control valve from a main line, the present inventors focused on changing an oil hydraulic unit itself as an oil hydraulic source and examined various oil hydraulic units as alternatives to a conventional oil hydraulic pump by comparison. As a result, the present inventors have found the following matters.

First, a servo motor driven pump is used effectively as an oil hydraulic drive source for a booster cylinder. The servo motor driven pump can operate while rotating at a frequency responsive to a required pressure condition and a required flow rate condition to prevent the occurrence of wasteful power loss. Second, the flow rate of an oil hydraulic pump is generally reduced with increase in a pressure. By contrast, the pressure and the flow rate of the servo motor driven pump are adjustable in a wide range and one servo motor driven pump of a dual-displacement type is capable of achieving the functions of two pumps: a low pressure and high flow rate pump and a high pressure and low flow rate pump. By using such a servo motor driven pump, particularly by using a plurality of such servo motor driven pumps in parallel, a large quantity of pressure oil is fed to the booster cylinder to increase the pressure of the cylinder effectively, particularly in an initial stage of pressure increase. Third, in a final stage of the pressure increase, a pressure can be increased to a hold-on pressure by selectively using one of the plurality of servo motor driven oil hydraulic pumps.

Specifically, by using the servo motor driven pump as the oil hydraulic drive source for the booster cylinder and controlling the drive source by feedback based on a pressure on an output side of the booster cylinder, even if test pipes have a variety of sizes or thicknesses, etc., requested pressure increase can be achieved only through setting of a hold-on pressure and a holding time required for each test pipe. This eliminates the burden of setting a pressure increasing speed and a change point of the pressure increasing speed for each difference in a size between pipes and each difference in a hold-on pressure. Further, a pump operates only during pressure increase and no pressure oil needs to be released during this pressure increase to cause practically no power loss.

More specifically, assuming that the performance of the servo motor driven pump is 20 MPa, the boosting ratio (pressure-receiving area ratio) of the booster cylinder is 2, a hold-on pressure is 30 MPa, and a holding time is 10 seconds, controlling the servo motor driven pump by feedback based on a water pressure on the output side of the booster cylinder makes the servo motor driven pump increase a pressure on an input side of the booster cylinder automatically before a water pressure on the output side of the booster cylinder becomes 30 MPa (before an oil pressure on the input side of the booster cylinder becomes 15 MPa), and then hold the increased pressure for the set holding time (10 seconds).

At this time, in a low-pressure period in an initial stage of the pressure increase, the servo motor driven pump supplies pressure oil at a relatively low pressure to the input side of the booster cylinder without stopping to alleviate the influence of pressure absorption by air remaining in a test pipe. In a subsequent pressure increasing period, the servo motor driven pump supplies pressure oil at a relatively high pressure continuously to the input side of the booster cylinder to increase the pressure on the output side. In this way, a pressure can be increased in a short time. In particular, if the servo motor driven pump is a dual-displacement pump, the servo motor driven pump has two modes including a low pressure and high flow rate mode and a high pressure and low flow rate mode. A pressure can be increased at a higher speed by making a switch between these two modes.

By connecting a plurality of servo motor driven pumps in parallel with respect to the booster cylinder and driving these servo motor driven pumps simultaneously, a flow rate can be increased. This contributes to further reduction in a time of pressure increase. However, if the plurality of servo motor driven pumps operates simultaneously to a point when a hold-on pressure is achieved, these servo motor driven pumps fail to operate in a perfectly-synchronized manner. This causes operation failure due to the imperfect synchronization in an end stage of the pressure increase (immediately before the hold-on pressure is achieved), making it difficult to control a pressure accurately. Thus, in the end stage of the pressure increase (immediately before the hold-on pressure is achieved), stopping the servo motor driven pumps except one and increasing a pressure using the one servo motor driven pump is an effective way in terms of control accuracy.

Regarding the booster cylinder, a pressure can be increased to a hold-on pressure using one cylinder if the hold-on pressure is low. However, if a hold-on pressure is high, increasing a pressure to this hold-on pressure using one cylinder inevitably involves a higher boosting ratio of the cylinder. If the boosting ratio of the booster cylinder is low, the booster cylinder performs high-speed operation at a low pressure and a high flow rate. However, with increase in the boosting ratio, the booster cylinder operates at a higher pressure and a lower flow rate. This causes a problem not only in terms of increase in a cylinder size resulting from increase in a piston stroke but also in terms of extension of a cycle time resulting from reduction in a pressure increasing speed. These can be handled effectively by connecting a plurality of booster cylinders having different boosting ratios in parallel with respect to a test pipe and using these booster cylinders in stages in order of increasing boosting ratio.

More specifically, if the pressure of the oil hydraulic source is 20 MPa at a maximum and a hold-on pressure is 75 MPa at a maximum, a boosting ratio of 3.75 or more is required. If a pressure is to be increased using one booster cylinder, this booster cylinder is required to have a boosting ratio of 3.75 or more. In a situation where the pressure of the oil hydraulic source is limited, the flow rate of the booster cylinder of such a high boosting ratio becomes inevitably low for its high boosting ratio. This necessarily causes reduction in a pressure increasing speed.

In response, this booster cylinder is divided into a plurality of cylinders to increase a boosting ratio in stages. For example, a 20 MPa booster cylinder and a 75 MPa booster cylinder are used. In view of the maximum pressure of the oil hydraulic source being 20 MPa, the 20 MPa booster cylinder is set to have a boosting ratio of 1 and the 75 MPa booster cylinder is set to have a boosting ratio of 3.75 or more as originally intended. By doing so, a pressure can be increased at a high speed using the booster cylinder of the lower boosting ratio before a pressure on the output side of the booster cylinder reaches 20 MPa. For pressure increase to a level above 20 MPa, a pressure is increased at an originally intended speed. This reduces a time of pressure increase in a low-pressure period before 20 MPa is achieved. As a result, an entire time of pressure increase is reduced.

In particular, if the servo motor driven pump is used as a drive source, the booster cylinder of the lower boosting ratio used in an initial stage of pressure increase is driven mainly at a low pressure and a high flow rate. A pressure on an input side required at the start of the pressure increase (the pressure of the oil hydraulic source) drops to about 5 (20/3.75) MPa. Thus, the booster cylinder of the higher boosting ratio to be used thereafter is also driven at a low pressure and a high flow rate at least at the beginning of the pressure increase. As a result, a time of the pressure increase is reduced further. In this regard, the servo motor driven pump adjustable in a wide range in terms of a pressure and a flow rate is used significantly effectively as an oil hydraulic source for a plurality of booster cylinders formed by dividing one booster cylinder. A dual-displacement servo motor driven pump adjustable in a particularly wide range in terms of a pressure and a flow rate is a more effective pump.

If three booster cylinders including a 20 MPa booster cylinder, a 40 MPa booster cylinder, and a 75 MPa booster cylinder are used, the boosting ratio of the 40 MPa booster cylinder is 2. As a result, a time of pressure increase is reduced in a middle-pressure period from 20 to 40 MPa in addition to the low-pressure period before 20 MPa is achieved. As a result, an entire time of pressure increase is reduced further.

By employing the aforementioned switching between the operation modes for the plurality of servo motor driven pumps and the aforementioned change in the number of servo motor driven pumps to operate, even if test pipe have sizes varying widely from 8-inch diameter to 24-inch diameter or more, a pressure in each test pipe can be increased to a hold-on pressure accurately and economically in a short time and the hold-on pressure can be held only through the simple setting operation of setting the hold-on pressure and a holding time.

A water hydraulic test method of this invention has been completed based on the aforementioned knowledge. In a water hydraulic test method of conducting a water hydraulic test on a manufactured metal pipe by increasing a pressure in the test pipe to a predetermined hold-on pressure by supplying high-pressure water forcibly from an oil hydraulically driven booster cylinder into the test pipe, a plurality of servo motor driven pumps connected in parallel is used as an oil hydraulic drive source for the booster cylinder. Before a pressure on an output side of the booster cylinder reaches a pressure near the hold-on pressure set in advance, the plurality of servo motor driven pumps operates simultaneously. After the pressure on the output side reaches the pressure near the hold-on pressure, the plurality of servo motor driven pumps stops operating except one and the pressure on the output side of the booster cylinder is increased to the hold-on pressure by operation of the one servo motor driven pump.

According to the water hydraulic test method of this invention, the oil hydraulic drive source for the booster cylinder employs a multi-servo pump system using a plurality of servo motor driven pumps combined in parallel. As a result, a time of pressure increase is reduced. More specifically, before a pressure on the output side of the booster cylinder reaches the pressure near the hold-on pressure set in advance, the plurality of servo motor driven pumps operates simultaneously at a low pressure and a high flow rate at the beginning and at a high pressure and a low flow rate thereafter while producing an output as large as possible at intervals. As a result, a large quantity of high-pressure water is supplied into the test pipe to increase a pressure in the test pipe at a high speed while the influence of air remaining in the test pipe is alleviated. Next, only in a short end period before the pressure on the output side of the booster cylinder reaches the hold-on pressure, only the one servo motor driven pump operates. This prevents operation failure due to imperfect synchronization that might occur in the multi-servo pump system. As a result, the pressure in the test pipe can be increased to the hold-on pressure at a high speed accurately and stably. Using the servo motor driven pump does not cause release of pressure oil, so that power loss is not caused both in a pressure increasing period and a period when a pressure is not increased.

The water hydraulic test method may actually be implemented as follows. A switching point pressure lower by a predetermined pressure (1 MPa, for example) than the hold-on pressure is set. The water pressure of high-pressure water is measured on the output side of the booster cylinder during pressure increase. The plurality of servo motor driven pumps operates simultaneously before the measured water pressure reaches the switching point pressure. When the measured water pressure reaches the switching point pressure, the plurality of servo motor driven pumps stops operating except one. When the measured pressure reaches the hold-on pressure, the one servo motor driven pump in operation is stopped. Thus, required setting operation is only to set the hold-on pressure and a holding time, so that the setting operation can be simplified significantly.

The servo motor driven pump operates in a wide range. Thus, the servo motor driven pump is adjustable in a wide range in terms of an oil pressure and an oil quantity. In the case of a low pressure, the servo motor driven pump can supply pressure oil to the low-pressure side of the booster cylinder at a high flow rate. In the case of a high pressure, the servo motor driven pump can supply pressure oil to the low-pressure side of the booster cylinder at a low flow rate. According to the servo motor driven pump of a dual-displacement type adjustable in a particularly wide range, a plurality of such servo motor driven pumps operates in the high pressure and high flow rate mode in an initial stage of pressure increase for reason of a low water pressure in the test pipe. As a result, high-pressure water can be supplied in a short time into the test pipe. If the test pipe has a small size or thickness, the quantity of the high-pressure water to be supplied is small and a hold-pressure is low. Thus, the plurality of servo motor driven pumps continues operating in the low pressure and high flow rate mode to achieve increase to a pressure near the hold-on pressure. From the pressure near the hold-on pressure, one servo motor driven pump operates in the high pressure and low flow rate mode to finally increase a pressure in the pipe to the hold-on pressure with high accuracy.

If the test pipe has a large size or thickness, the plurality of servo motor driven pumps continues operating in the low pressure and high flow rate mode even after an initial stage of pressure increase to continue supplying a large quantity of high-pressure water. Then, high-pressure water is supplied in the high pressure and low flow rate mode. From a pressure near a hold-on pressure, one servo motor driven pump operates in the high pressure and low flow rate mode to increase a pressure in the test pipe to the hold-on pressure. If the test pipe has a middle size, timing of switching from the low pressure and high flow rate mode to the high pressure and low flow rate mode after an initial stage of pressure increase is changed in various ways.

The following describes a reason why one pump operates in an end stage of pressure increase from a pressure near a hold-on pressure. A plurality of servo motor driven pumps is difficult to operate in a perfectly-synchronized manner. Hence, if these servo motor driven pumps operate simultaneously in a final stage of pressure increase at a high pressure and a low flow rate, imperfect synchronization becomes obvious for an extremely low flow rate. This causes secondary adverse effect such as hunting to make it difficult to achieve pressure increase smoothly and accurately in the final stage. Even with one operating pump, a pressure in the pipe is still increased promptly at a high pressure and a low flow rate. A low flow rate has an advantage in terms of accurate control.

Regarding the booster cylinder, the number of booster cylinders may be one. However, in consideration of a case where a hold-on pressure is set in a wide range and a maximum of the hold-on pressure is considerably high compared to the pressure of the oil hydraulic source, for example, using a plurality of booster cylinders is more desirable. More specifically, it is preferable that a plurality of booster cylinders having respective boosting ratios increasing in stages be arranged in parallel with respect to the test pipe and that the booster cylinders be used in turn in order of increasing boosting ratio. Using the booster cylinders in turn and in stages in order of increasing boosting ratio increases a pressure at a higher speed on a low-pressure side or on the low-pressure side and a middle-pressure side than using only a booster cylinder of a high boosting ratio, so that a time of pressure increase is reduced.

The water hydraulic test device of this invention attempts to reduce a time of pressure increase further by a combination of the multi-servo pump system using a plurality of servo motor driven pumps and a multi-cylinder system of using a plurality of booster cylinders. More specifically, a plurality of servo motor driven pumps used as an oil hydraulic drive source for a booster cylinder is connected in parallel with respect to the booster cylinder. The booster cylinder includes a plurality of booster cylinders connected in parallel with respect to a test pipe. The booster cylinders have respective boosting ratios increasing in stages. A switching mechanism is provided between the oil hydraulic source and the plurality of booster cylinders. The switching mechanism supplies pressure oil from the oil hydraulic source selectively to one of the plurality of booster cylinders.

In an actual case of the water hydraulic test device, a water hydraulic sensor used for measuring the water pressure of high-pressure water is desirably provided in a line on an output side of the booster cylinder. The water hydraulic test device desirably comprises a cylinder control system that controls the switching mechanism based on a water pressure measured using the water hydraulic sensor in such a manner that the booster cylinders operate in turn in order of increasing boosting ratio.

A water hydraulic sensor used for measuring the water pressure of high-pressure water is desirably provided in a line on an output side of the booster cylinder. The water hydraulic test device desirably comprises a pump control system that controls the plurality of servo motor driven pumps in such a manner that the plurality of servo motor driven pumps operates simultaneously before a measured water pressure reaches a switching point pressure lower by a predetermined pressure (1 MPa, for example) than a hold-on pressure, and that one of the servo motor driven pumps operates thereafter before the measured pressure reaches the hold-on pressure.

According to the aforementioned control systems, pressure oil is initially supplied from the plurality of servo motor driven pumps to a booster cylinder of a lowest boosting ratio. When a measured water pressure reaches a pressure near a maximum water pressure of this booster cylinder, pressure oil is supplied to a booster cylinder of a next higher boosting ratio. Such supply of pressure oil continues sequentially to increase a pressure in the test pipe to a pressure near the hold-on pressure using the plurality of servo motor driven pumps. The pressure in the test pipe is thereafter increased using one servo motor driven pump.

Advantageous Effects of Invention

According to the water hydraulic test method of this invention, to oil hydraulically drive the booster cylinder from which high-pressure water is supplied into the test pipe, the multi-pump system is employed according to which a plurality of servo motor driven pumps arranged in parallel is used as an oil hydraulic source and the number of pumps to operate is changed appropriately in a manner that depends on a stage of pressure increase. Thus, even if the test pipe has a wide range of sizes and a test pressure and a time of holding the test pressure change in various ways, a pressure in the test pipe can be increased accurately to the test pressure through simple setting operation. This makes it possible to conduct various types of water hydraulic tests using one test device and the resultant rationality of the test device achieves numerous effects. Further, as a result of reducing a cycle time, the number of test pipes to be tested per unit time is increased and the resultant rationality also achieves significant effect. Additionally, the occurrence of power loss is reduced effectively to achieve the effect of largely reducing cost relating to power. In this way, the water hydraulic test method of this invention works significantly effectively in reducing cost required for a water hydraulic test.

The water hydraulic test device of this invention employs the multi-cylinder system in addition to the aforementioned multi-pump system. According to the multi-cylinder system, a plurality of booster cylinders having respective boosting ratios increasing in stages operates in turn in order of increasing boosting ratio. This contributes to further reduction in a test time and works more effectively in reducing cost required for a water hydraulic test.

EMBODIMENT FOR CARRYING OUT INVENTION

An embodiment of this invention is described below. A water hydraulic test method and a water hydraulic test device of this embodiment are used for conducting a water hydraulic test on an electric resistance welded pipe manufactured on an electric resistance welded pipe manufacturing line.

Figure 1:
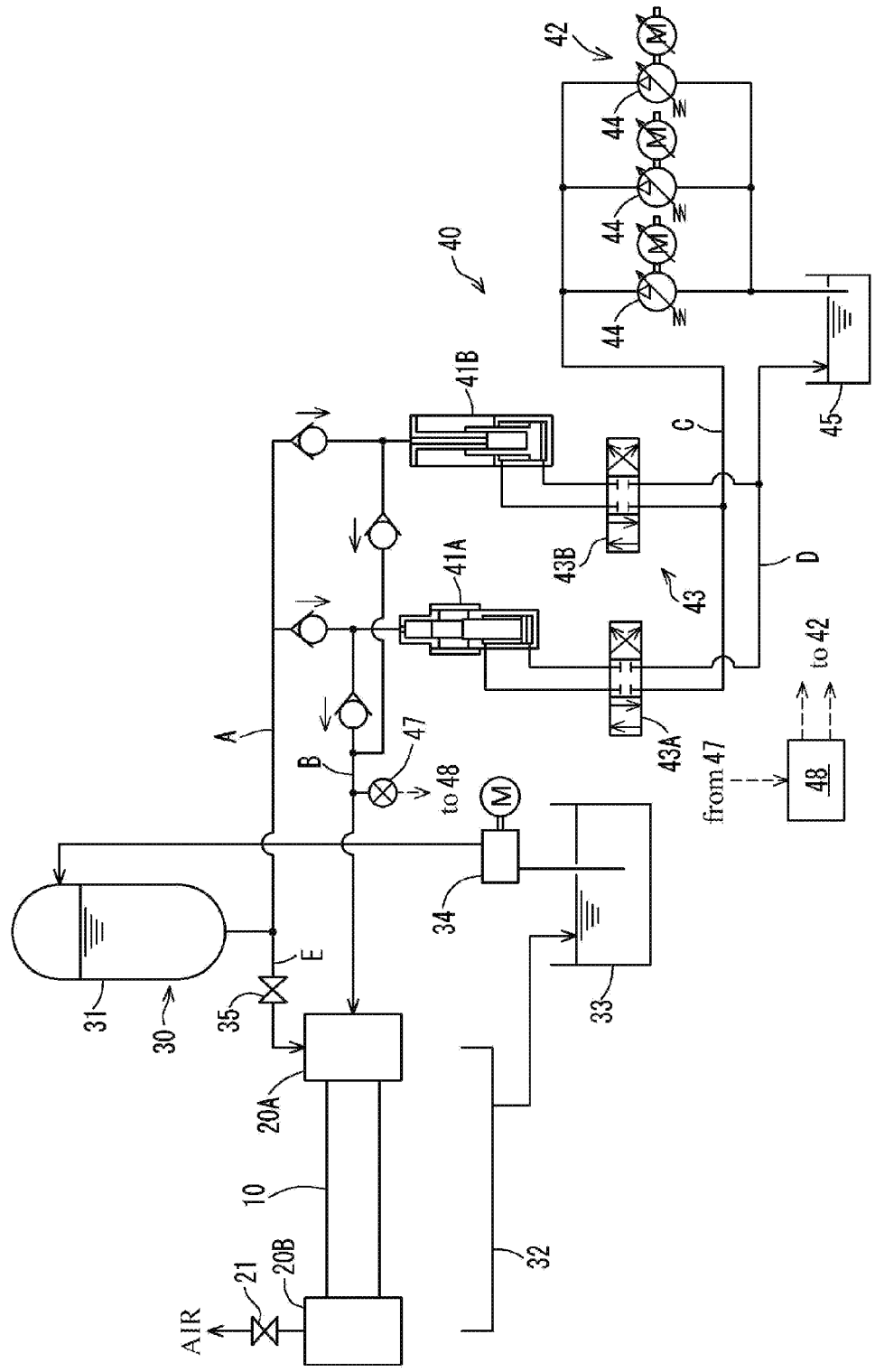
FIG. 1 shows the structure of a water hydraulic test device employed suitably for implementing a method of a water hydraulic test of this invention and shows fluid distribution.

As shown in FIG. 1, the water hydraulic test device of this embodiment is used for checking the quality of an electric resistance welded pipe 10 (hereinafter called a test pipe 10) to be subjected to a water hydraulic test at a welded part (seam part) of the test pipe 10, etc., by putting the test pipe 10 between a headstock unit 20A as a fixed head and a tailstock unit 20B as a movable head, pouring water into the pipe to fill the pipe entirely with water, and then supplying high-pressure water into the pipe. The water hydraulic test device includes a low-pressure water supply system 30 that pours a large quantity of water in a non-pressurized condition (at a normal pressure) or at a low pressure into the test pipe 10, and a high-pressure water supply system 40 that forcibly supplies high-pressure water under pressure into the test pipe 10 after the test pipe 10 is full of the non-pressurized water or the low-pressure water.

The low-pressure water supply system 30 is to pour water in a water tank 31 installed in a higher position that a position where the test pipe 10 is set into the test pipe 10 without stopping by means of the self weight of the water or a low pressure of 1 MPa or less (about 0.8 MPa, for example). More specifically, after a test is conducted, water ejected from the test pipe 10 is stored once in a pool 32 below the test pipe 10 and transferred to a settlement tank not shown in the drawings. Then, a supernatant of the water is stored in a water sump 33. The water in the water sump 33 is drawn up by a pump 34 through a filter into the tank 31 in the higher position and then poured into the test pipe 10 through the headstock 20A. At this time, air in the test pipe 10 is exhausted through an air extraction valve 21 provided to the tailstock 20B. A cylinder type on-off valve 35 is placed in a line E extending from the water tank 31 to the headstock 20A.

The high-pressure water supply system 40 is to forcibly supply water at a high pressure of 75 MPa at a maximum into the test pipe 10 full of water using a booster cylinder 41A and a booster cylinder 41B of an oil hydraulic system. The booster cylinders 41A and 41B of the oil hydraulic system are arranged in parallel with respect to the test pipe 10 and driven selectively by a drive system 42. To drive the booster cylinders 41A and 41B selectively, a solenoid valve 43A and a solenoid valve 43B forming a switching mechanism 43 are interposed between the booster cylinder 41A and the drive system 42 and between the booster cylinder 41B and the drive system 42, respectively.

The first booster cylinder 41A is a low-pressure cylinder producing a pressure of 21 MPa at a maximum. The second booster cylinder 41B is a high-pressure cylinder producing a pressure of 75 MPa at a maximum. Each of these cylinders has a piston to be caused to move back and forth by pressure oil supplied from the drive system 42. If the piston is caused to retract, water is sucked into an output side from the inside of the tank 31 through a line A. If the piston is caused to advance, the sucked water is pressurized and supplied through a line B to the headstock 20A, thereby supplying the high-pressure water forcibly into the test pipe 10 full of water.

The drive system 42 for the booster cylinders 41A and 41B includes a plurality of servo motor driven pumps 44 arranged in parallel as principal components. One of the plurality of servo motor driven pumps 44 is a main pump and the remaining pump is a secondary pump. All these servo motor driven pumps 44 are dual-displacement pumps. These servo motor driven pumps 44 are driven simultaneously and then the main pump is driven alone to automatically increase a water pressure on an output side of each of the booster cylinders 41A and 41B to a target value. For this automatic pressure increase, the water pressure on the output side of each of the booster cylinders 41A and 41B (line B) is measured using a water hydraulic sensor 47 and the measured water pressure is transmitted to a controller 48 functioning both as a cylinder control system and a pump control system. In this way, switching control of the switching mechanism 43, and output control and switching control of the servo motor driven pumps 44 are executed.

The switching control of the switching mechanism 43 includes on-off switching control of the booster cylinders 41A and 41B and forward-reverse switching control of a cylinder in an on condition. The on-off switching control of the booster cylinders 41A and 41B is to place one of the solenoid valves 43A and 43B forming the switching mechanism 43 in an open condition and the other valve in a closed condition, thereby supplying pressure oil from the drive system 42 to one of the booster cylinders 41A and 41B and making the cylinder supplied with the pressure oil perform forward operation or reverse operation. The forward-reverse switching control is to make a switch between forward operation and reverse operation of one of the booster cylinders 41A and 41B in an operating condition. The forward-reverse switching control is described as follows.

The servo motor driven pumps 44 are driven to pressurize oil in an oil sump 45 and discharge the pressure oil. The discharged pressure oil passes through one of the solenoid valves 43A and 43B in an open condition (forward direction) and is then supplied from a line C to an input side (inlet) of one of the booster cylinders 41A and 41B. As a result, a piston in one of the booster cylinders 41A and 41B is caused to advance to discharge high-pressure water from an output side thereof. As described above, this high-pressure water is fed to the headstock 20A. As the piston is caused to advance, the oil is ejected from the input side (outlet). This oil goes from one of the solenoid valves 43A and 43B, passes through a line D, and then returns to the oil sump 45.

By changing the operation of one of the solenoid valves 43A and 43B in an open condition from a forward direction to a reverse direction, oil in the oil sump 45 is supplied through the line C to the input side (outlet) of one of the booster cylinders 41A and 41B to cause the piston thereof to retract. As the piston is caused to retract, the oil is ejected from the input side (inlet). This oil goes from one of the solenoid valves 43A and 43B, passes through the line D, and then returns to the oil sump 45.

The water hydraulic test method of this embodiment is conducted using the aforementioned water hydraulic test device. The following describes the function of the water hydraulic test device of this embodiment and the water hydraulic test method of this embodiment.

Figure 2:
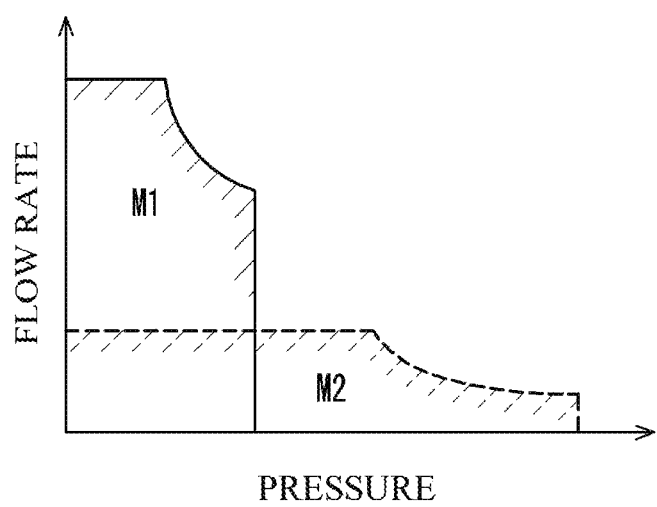
FIG. 2 is a graph showing an available range of a servo motor driven pump used as a booster cylinder drive source in the water hydraulic test device and showing a relationship between a discharge pressure and a discharge flow rate.
Figure 5:
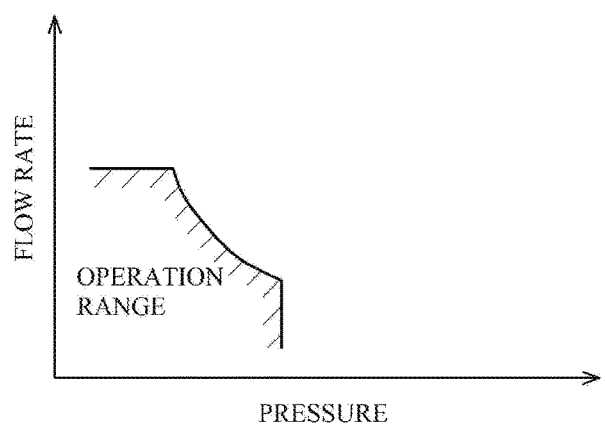
FIG. 5 is a graph showing an available range of an oil hydraulic pump used as the booster cylinder drive source of FIG. 4 and showing a relationship between a discharge pressure and a discharge flow rate.
Figure 6:
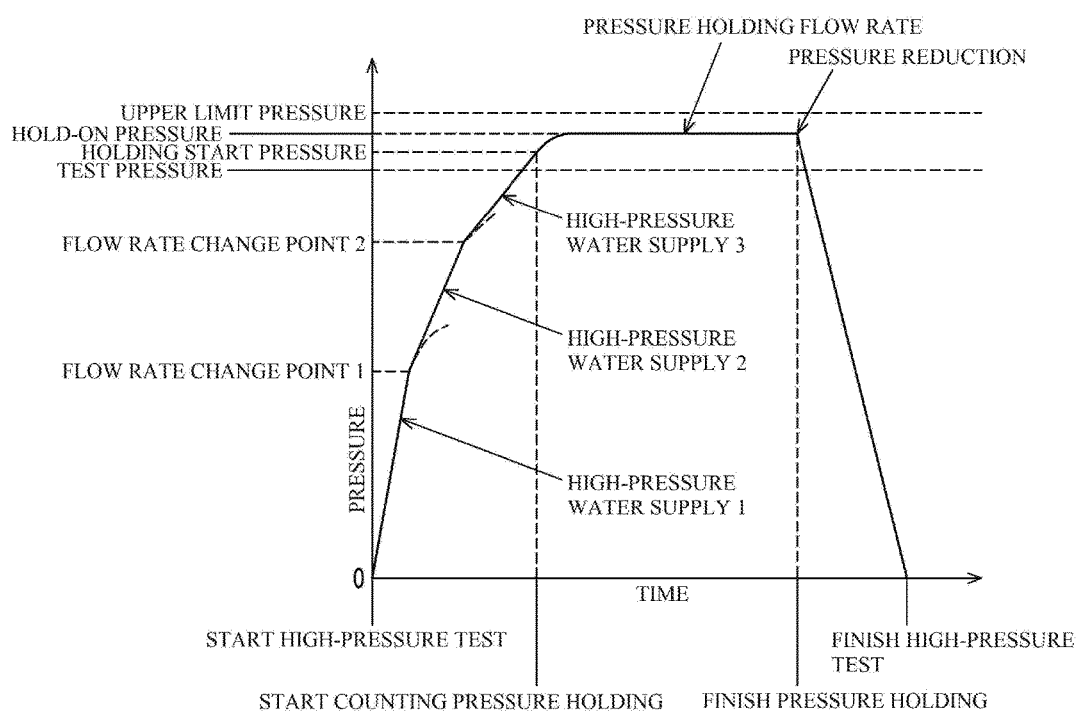
FIG. 6 is a graph showing temporal change in a water pressure in a pipe observed in a conventional water hydraulic test.
Figure 7:
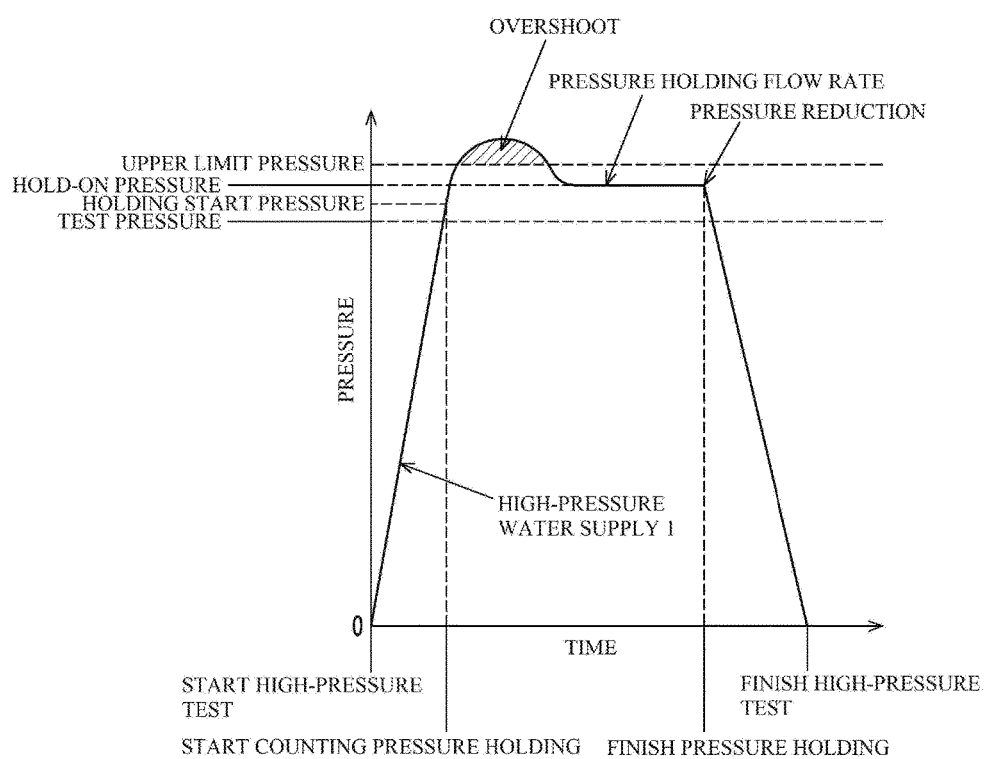
FIG. 7 is a graph showing temporal change in a water pressure in a pipe observed in the conventional water hydraulic test.

The servo motor driven pump 44 forming the principal part of the drive system 42 includes a single-displacement model and a dual-displacement model. Here, a dual-displacement pump is used. According to the dual-displacement model, as shown in FIG. 2, the capacity of a variable displacement pump is switched to permit switching from a low pressure and high flow rate mode M1 to a high pressure and low flow rate mode M2 and from the high pressure and low flow rate mode M2 to the low pressure and high flow rate mode M1. This allows the servo motor driven pump 44 to adjust a relationship between a pressure and a flow rate in a considerably wider range from a low pressure and a high flow rate to a high pressure and a low flow rate than a general oil hydraulic pump to be driven by an AC motor (FIG. 5).

In a first stage of a water hydraulic test on the test pipe 10 as a manufactured electric resistance welded pipe, the test pipe 10 is set on a test line and put between the headstock 20A and the tailstock 20B. In a second stage, while the water tank 31 in the low-pressure water supply system 30 is filled with water, the cylinder type on-off valve 35 in the line E is switched from a closed condition to an open condition. As a result, the water in the tank 30 is poured into the test pipe 10 through the line E without stopping by means of the self weight of the water or a low pressure of 1 MPa or less. After the test pipe 10 becomes full of the water as a result of pouring of the water into the test pipe 10 from the water tank 31, water at a high pressure of 75 MPa at a maximum is supplied from the high-pressure water supply system 40 into the test pipe 10 in a third stage. This increases a pressure in the test pipe 10 to a test water pressure required for the water hydraulic test. This test water pressure is held for a holding time required for the water hydraulic test. These operations differ in a manner that depends on a test pressure required for the test pipe 10. The test pressure corresponds to a hold-on pressure, so that these pressures have the same meaning.

The following describes operation of supplying high-pressure water by the high-pressure water supply system 40 and operation of increasing a pressure in the test pipe 10 through the operation of supplying high-pressure water. These operations are described for each test pressure. Three servo motor driven pumps 44 are used. One of the servo motor driven pumps 44 is a main pump and the two are secondary pumps. All of these pumps apply a pressure of 21 MPa at a maximum. The low-pressure booster cylinder 41A applies a pressure of 21 MPa at a maximum and has a boosting ratio (pressure-receiving area ratio) of 1. The high-pressure booster cylinder 41B applies a pressure of 75 MPa at a maximum and has a boosting ratio (pressure-receiving area ratio) of 3.57.

If a test pressure (hold-on pressure) is 21 MPa or less, by setting the test pressure (hold-on pressure) and a holding time at the controller 48, the drive system 42 is operated in a first stage so as to cause the low-pressure booster cylinder 41A to retract. More specifically, while the solenoid valve 43A corresponding to the booster cylinder 41A is opened in the reverse direction and the solenoid valve 43B corresponding to the booster cylinder 41B is closed, the three servo motor driven pumps 44 in the drive system 42 operate simultaneously at a maximum output or an output near the maximum output. In response to the retracting motion of the booster cylinder 41A, water is sucked into the output side of the booster cylinder 41A from the water tank 31. Then, in a second stage, the solenoid valve 43A is switched from the reverse direction to the forward direction to cause the booster cylinder 41A to start advancing.

At the start of the advancing motion of the booster cylinder 41A, an oil pressure is low at the input side thereof. Thus, the dual-displacement servo motor driven pumps 44 operate in the low pressure and high flow rate mode to supply a large quantity of pressure oil forcibly in a short time to the input side of the booster cylinder 41A. As a result, a large quantity of pressure water is supplied forcibly from the output side of the booster cylinder 41A into the test pipe 10 full of water through the line B and further through the headstock 20A. As a result of the forcible supply of pressure oil to the input side of the booster cylinder 41A and the resultant supply of pressure water into the test pipe 10, a water pressure on the output side of the booster cylinder 41A is increased to further increase an oil pressure on the input side of the booster cylinder 41A. Then, the dual-displacement servo motor driven pumps 44 are shifted from the low pressure and high flow rate mode to the high pressure and low flow rate mode to continue supplying pressure oil to the input side of the booster cylinder 41A while increasing the pressure of the pressure oil. As a result, pressure water is supplied from the output side of the booster cylinder 41A into the test pipe 10 while the pressure of the supplied water is increased.

Figure 3:
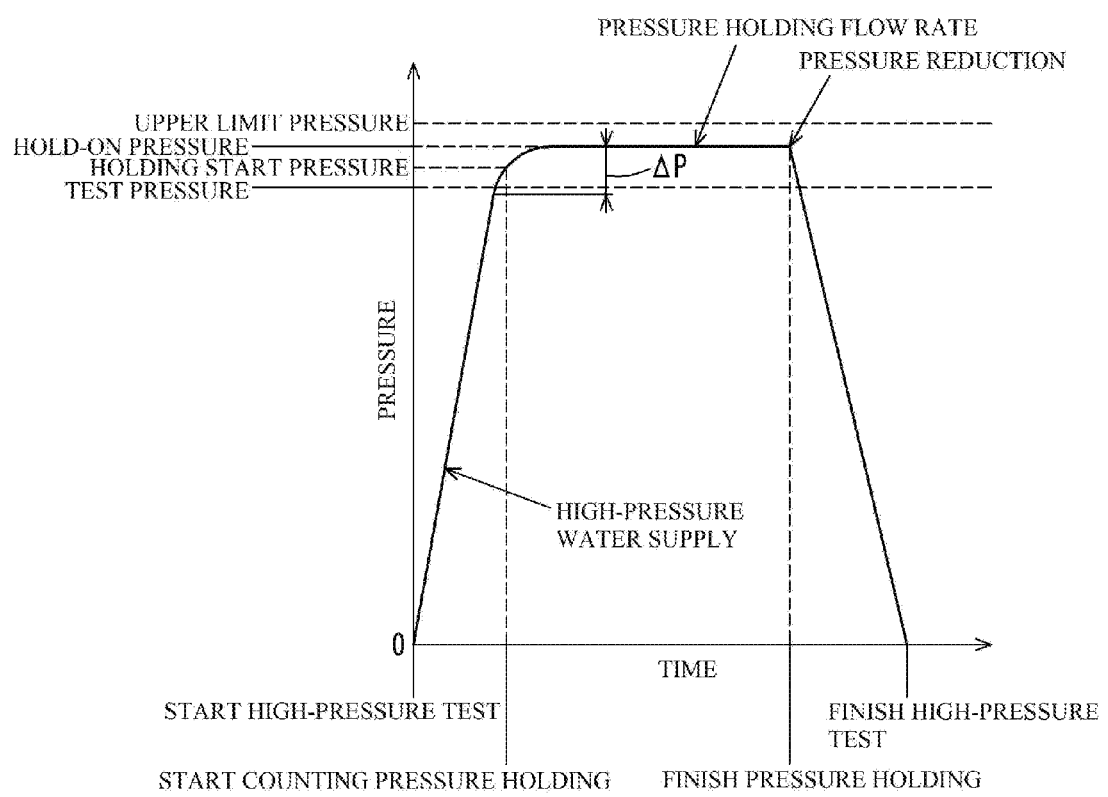
FIG. 3 is a graph showing temporal change in a water pressure in a pipe observed in the water hydraulic test.
Figure 4:
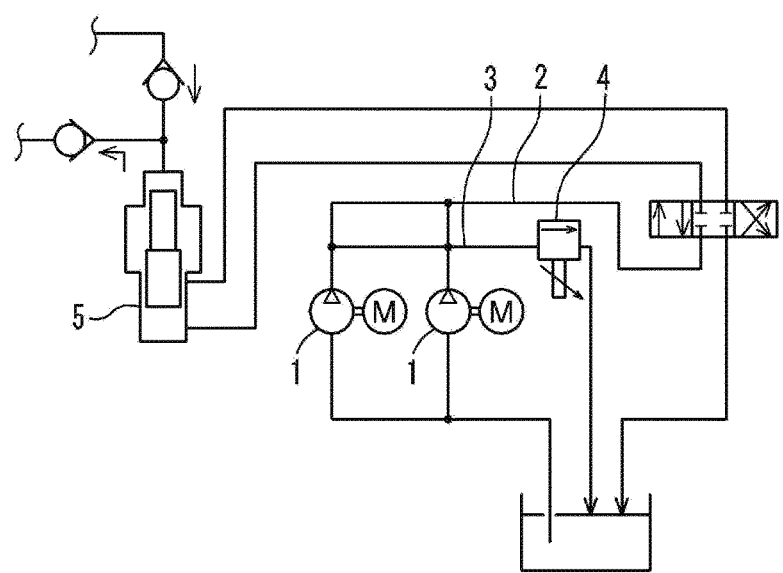
FIG. 4 is an oil hydraulic circuit diagram showing a booster cylinder drive source in a water hydraulic test device used for implementing a conventional water hydraulic test method.

As shown in FIG. 3, in response to the supply of pressure water into the test pipe 10, a pressure in the test pipe 10 is increased. The inner pressure of the test pipe 10 is monitored using the water hydraulic sensor 47 provided on the output sides of the booster cylinders 41A and 41B (in the line B). If the inner pressure reaches a switching point pressure lower than a holding start pressure and lower than the set hold-on pressure by AP (AP is a fixed value and here, 1 MPa), the secondary pumps among the three servo motor driven pumps 44 are stopped and only the main pump continues operating. The main pump continues operating in the high pressure and low flow rate mode M2 (see FIG. 2) to increase the inner pressure of the test pipe 10 to the set hold-on pressure.

If the pressure in the test pipe 10 reaches the set hold-on pressure, the set pressure is held for a predetermined time and the test is finished. Next, a pressure reducing valve provided to the headstock 20A, to the tailstock 20B, or to each of the headstock 20A and the tailstock 20B is opened to reduce the pressure in the pipe. After the pressure reduction is finished, the tailstock 20B is removed from the test pipe 10 and the test pipe 10 is further removed from the fixed tailstock 20A. Then, the test pipe 10 is tilted to discharge water in the pipe in its entirety into the pool 32 below the pipe. As described above, part of the discharged water is recycled for a next test.

If the test pressure (hold-on pressure) exceeds 21 MPa and does not exceed 75 MPa, the test pressure (hold-on pressure) and a holding time are set at the controller 48. Then, in a first stage, the drive system 42 is operated so as to cause the low-pressure booster cylinder 41A and the high-pressure booster cylinder 41B to retract. More specifically, while the solenoid valves 43A and 43B corresponding to the booster cylinders 41A and 41B respectively are opened in the reverse direction, the three servo motor driven pumps 44 in the drive system 42 operate simultaneously at a maximum output or an output near the maximum output. In response to the retracting motions of the booster cylinders 41A and 41B, water is sucked into the respective output sides of the booster cylinders 41A and 41B from the water tank 31. Then, in a second stage, the solenoid valve 43A is switched from the reverse direction to the forward direction and the solenoid valve 43B is switched from the open condition in the reverse direction to a closed condition. As a result, only the booster cylinder 41A starts advancing.

At the start of the advancing motion of the booster cylinder 41A, an oil pressure is low at the input side thereof. Thus, the dual-displacement servo motor driven pumps 44 operate in the low pressure and high flow rate mode to supply a large quantity of pressure oil forcibly in a short time to the input side of the booster cylinder 41A. As a result, a large quantity of pressure water is supplied forcibly from the output side of the booster cylinder 41A into the test pipe 10 full of water through the line B and the headstock 20A. As a result of the forcible supply of pressure oil to the input side of the booster cylinder 41A and the resultant supply of pressure water into the test pipe 10, a water pressure on the output side of the booster cylinder 41A is increased to further increase an oil pressure on the input side of the booster cylinder 41A. Then, the dual-displacement servo motor driven pumps 44 are shifted from the low pressure and high flow rate mode to the high pressure and low flow rate mode to continue supplying pressure oil to the input side of the booster cylinder 41A while increasing the pressure of the pressure oil. As a result, pressure water is supplied from the output side of the booster cylinder 41A into the test pipe 10 while the pressure of the supplied water is increased.

In response to the supply of pressure water into the test pipe 10, a pressure in the test pipe 10 is increased. The pressure in the test pipe 10 is monitored using the water hydraulic sensor 47 provided on the output sides of the booster cylinders 41A and 41B (in the line B). If the pressure in the test pipe 10 reaches 21 MPa, the solenoid valve 43A is switched from the open condition in the forward direction to a closed condition, whereas the solenoid valve 43B is switched from the closed condition to an open condition in the forward direction. In response, the low-pressure booster cylinder 41A stops advancing and the high-pressure booster cylinder 41B in turn starts advancing.

The high-pressure booster cylinder 41B has a boosting ratio of 3.57. Thus, while the servo motor driven pumps 44 produce a pressure of 21 MPa at a maximum, a water pressure on the output side can be increased to 75 MPa. At the time of switching to the high-pressure booster cylinder 41B, a water pressure on the output side has been increased to 21 MPa. Thus, the servo motor driven pumps 44 are to be substantially responsible for pressure increase from 5.9 (21/3.57) MPa. For such a low pressure, the servo motor driven pumps 44 again start to operate in the low pressure and high flow rate mode M1. In response, a large quantity of pressure oil starts to be supplied again into the input side of the booster cylinder 41B. The booster cylinder 41B has a high boosting ratio of 3.57 to result in a low flow rate correspondingly on the output side thereof. Meanwhile, a high flow rate on its input side compensates for the flow rate on the high pressure side. Thus, while the flow rate on the output side of the booster cylinder 41B is lower than that on the output side of the booster cylinder 41A, a difference between these flow rates is small. As a result, a large quantity of pressure water is supplied forcibly from the output side of the booster cylinder 41B into the test pipe 10 through the line B and the headstock 20A, thereby increasing a pressure in the test pipe 10 further.

As a result of the forcible supply of pressure oil to the input side of the booster cylinder 41B and the resultant supply of pressure water into the test pipe 10, a water pressure on the output side of the booster cylinder 41A is increased to further increase an oil pressure on the input side of the booster cylinder 41A. Then, the dual-displacement servo motor driven pumps 44 are shifted from the low pressure and high flow rate mode to the high pressure and low flow rate mode to continue supplying pressure oil to the input side of the booster cylinder 41B while increasing the pressure of the pressure oil further. As a result, pressure water is supplied from the output side of the booster cylinder 41B into the test pipe 10 while the pressure of the supplied water is increased further, thereby increasing a water pressure in the test pipe 10 further.

If the water pressure in the test pipe 10 reaches the switching point pressure lower than the holding start pressure and lower than the set hold-on pressure by AP (here, 1 MPa), the secondary pumps among the three servo motor driven pumps 44 are stopped and only the main pump continues operating. The main pump continues operating in the high pressure and low flow rate mode M2 to increase the inner pressure of the test pipe 10 to the set hold-on pressure.

If the pressure in the test pipe 10 reaches the set hold-on pressure, the set hold-on pressure is held for a predetermined time and the test is finished. Next, the pressure reducing valve provided to the headstock 20A, to the tailstock 20B, or to each of the headstock 20A and the tailstock 20B is opened to reduce the pressure in the pipe 10. After the pressure reduction is finished, the tailstock 20B is removed from the test pipe 10 and the test pipe 10 is further removed from the fixed tailstock 20A. Then, the test pipe 10 is tilted to discharge water in the pipe in its entirety into the pool 32 below the pipe. As described above, part of the discharged water is recycled for a next test.

According to the aforementioned water hydraulic test method, particularly the method of increasing a pressure in the test pipe 10, once a hold-on pressure and a holding time are set at the controller 48, the controller 48 executes control automatically in a manner that depends on a water pressure on each of the output sides of the booster cylinders 41A and 21B. Thus, even if test pipes 10 have a variety of sizes or thicknesses, the test pipes 10 of all sizes can be tested using one test device.

For conducting test on the test pipes 10 of various types using one device, a time required for a test on one test pipe 10 (cycle time) should be reduced. Such reduction in time can be achieved by the water hydraulic test method of this embodiment. Specifically, according to the water hydraulic test method of this embodiment, a pressure in the test pipe 10 is increased to a pressure near a set hold-on pressure using a plurality of oil hydraulic units. This makes it possible to supply a large quantity of high-pressure water into the test pipe 10 within a short time. Additionally, these oil hydraulic units are the dual-displacement servo motor driven pumps 44 having both the low pressure and high flow rate mode M1 and the high pressure and low flow rate mode M2. Thus, even if test pipes 10 have a variety of sizes or thicknesses including a thick test pipe 10 of an extremely large diameter exceeding 24 inches, absorption of a pressure caused by compression of remaining air in an initial stage of pressure increase can be compensated for in every test pipe 10. As a result, a pressure can be increased to the pressure near the set hold-on pressure in a shortest possible time.

Additionally, for increase from a pressure near a set hold-on pressure to the set hold-on pressure, only one of plurality of the servo motor driven pumps 44 operates alone in the high pressure and low flow rate mode M2 for convergence on the set hold-on pressure at a low flow rate. This avoids the risk of an overshoot. Further, a problem of hunting due to imperfect synchronization does not occur. As a result, convergence on the set hold-on pressure can be achieved with high accuracy.

In an entire period of a test and an entire period in which the test is not conducted, only a necessary quantity of pressure water is supplied to a low-pressure side of the booster cylinder 41 and substantially no pressure oil is released. Thus, practically no power loss is caused in an oil hydraulic unit.

As described above, according to the water hydraulic test method of this embodiment, test pipes 10 in a range from a small-diameter test pipe 10 to a large-diameter test pipe 10 can be subjected to a test using one water hydraulic test device. Further, a time required for each test is reduced, thereby increasing the number of pipes tested per unit time and reducing the occurrence of power loss in an oil hydraulic unit. These function to reduce cost significantly required for a test.

If a water pressure on an output side reaches the switching point pressure while the plurality of servo motor driven pumps 44 continues operating in the low pressure and high flow rate mode during supply of high-pressure water, the low pressure and high flow rate mode is not switched to the high pressure and low flow rate mode. When one servo motor driven pump 44 operates alone thereafter before a hold-on pressure is achieved, this servo-motor driven pump 44 continues operating in the low pressure and high flow rate mode.

EXAMPLES

Electric resistance welded steel pipes having outer diameters from 203 mm to 21 inches were actually tested by the aforementioned water hydraulic test method and results of the tests are described herein. The used electric resistance welded steel pipes conform to the API-X80 standard. Regarding a thickness, except a pipe of an outer diameter of 203 mm, two thicknesses including 5.0 mm and 12.7 mm were prepared for each outer diameter. The pipe of an outer diameter of 203 mm has one thickness of 12.7 mm. All pipes have a length of 1372 cm (13.72 m). A yield stress YS was set at 562 MPa between a minimum of 555 MPa and a maximum of 705 MPa. A test pressure P was determined using the yield stress YS and the specifications of the steel pipes. The test pressure P was calculated using the formula 1 as follows:

$$P = (2 \times \text{factor} f \times YS\text{min} \times \text{thickness} t)/\text{outer diameter } D \quad \text{[Formula 1]}$$

Table 1 shows the specifications and the test pressure P of each test pipe, and a required water quantity of each test pipe calculated based on the specifications and the test pressure P. Two types of the required water quantity are shown including a low-pressure water supply quantity and a high-pressure water supply quantity. The high-pressure water supply quantity shown in Table 1 includes a water quantity required for absorption of compression of remaining air, a water quantity required for absorption of expansion of a steep pipe, a water quantity required for pressure increase to 21 MPa, a water quantity required for pressure increase from 21 MPa to a test pressure, and a total of these water quantities. The total water quantity is divided into a water quantity to be supplied by a low-pressure booster cylinder and a water quantity to be supplied by a high-pressure booster cylinder. If a test pressure does not exceed 21 MPa, a water quantity required for pressure increase to 21 MPa means a water quantity required for pressure increase to the test pressure and a water quantity required for pressure increase from 21 MPa to the test pressure is zero.

The low-pressure booster cylinder has a maximum capacity of 95 L and the high-pressure booster cylinder has a maximum capacity of 40 L. Three 15-kW servo motor driven pumps were used. Here, air in an amount of 1.5% was assumed to remain in a test pipe. However, as described above, this amount inevitably varies widely. Thus, required water quantities calculated herein are rough indications. As described above, influence by this variation can be avoided by monitoring a water pressure on an output side of a booster cylinder during an actual test.

TABLE 1

| inch | O. D. (mm) | L (cm) | WT (mm) | factor f | X80 (MPa) | Test P (MPa) | P/S (kN) | low-pressure water supply quantity (l) | high-pressure water supply quantity (l) 1.5% remaining air | high-pressure water supply quantity (l) 0.5% expansion of steel pipe |
|---|---|---|---|---|---|---|---|---|---|---|
|  | 203.0 | 1372 | 12.7 | 1.0 | 562.0 | 70.3 | 228 | 444 | 7 | 2.2 |
| 8" | 219.1 | 1372 | 5.0 | 1.0 | 562.0 | 25.7 | 97 | 517 | 8 | 2.6 |
| 8" | 219.1 | 1372 | 12.7 | 1.0 | 562.0 | 65.2 | 246 | 517 | 8 | 2.6 |
| 9⅝" | 244.5 | 1372 | 5.0 | 1.0 | 562.0 | 23.0 | 108 | 644 | 10 | 3.2 |
| 9⅝" | 244.5 | 1372 | 12.7 | 1.0 | 562.0 | 58.4 | 274 | 644 | 10 | 3.2 |
| 10¾" | 273.1 | 1372 | 5.0 | 1.0 | 562.0 | 20.6 | 121 | 804 | 12 | 4.0 |
| 10¾" | 273.1 | 1372 | 12.7 | 1.0 | 562.0 | 52.3 | 306 | 804 | 12 | 4.0 |
| 12" | 323.8 | 1372 | 5.0 | 1.0 | 562.0 | 17.4 | 143 | 1,130 | 17 | 5.6 |
| 12" | 323.8 | 1372 | 12.7 | 1.0 | 562.0 | 44.1 | 363 | 1,130 | 17 | 5.6 |
| 14" | 355.6 | 1372 | 5.0 | 1.0 | 562.0 | 15.8 | 157 | 1,363 | 20 | 6.8 |
| 14" | 355.6 | 1372 | 12.7 | 1.0 | 562.0 | 40.1 | 399 | 1,363 | 20 | 6.8 |
|  | 377.0 | 1372 | 5.0 | 1.0 | 562.0 | 14.9 | 166 | 1,532 | 23 | 7.7 |
|  | 377.0 | 1372 | 12.7 | 1.0 | 562.0 | 37.9 | 423 | 1,532 | 23 | 7.7 |
| 16" | 406.4 | 1372 | 5.0 | 1.0 | 562.0 | 13.8 | 179 | 1,780 | 27 | 8.9 |
| 16" | 406.4 | 1372 | 12.7 | 1.0 | 562.0 | 35.1 | 456 | 1,780 | 27 | 8.9 |
|  | 426.0 | 1372 | 5.0 | 1.0 | 562.0 | 13.2 | 188 | 1,956 | 29 | 9.8 |
|  | 426.0 | 1372 | 12.7 | 1.0 | 562.0 | 33.5 | 478 | 1,956 | 29 | 9.8 |
| 20" | 508.0 | 1372 | 5.0 | 1.0 | 562.0 | 11.1 | 224 | 2,781 | 42 | 13.9 |
| 20" | 508.0 | 1372 | 12.7 | 1.0 | 562.0 | 28.1 | 570 | 2,781 | 42 | 13.9 |
| 21" | 530.0 | 1372 | 5.0 | 1.0 | 562.0 | 10.6 | 234 | 3,027 | 45 | 15.1 |
| 21" | 530.0 | 1372 | 12.7 | 0.8 | 562.0 | 20.2 | 446 | 3,027 | 45 | 15.1 |

| inch | high-pressure water supply quantity (l) 21 MPa Compressed quantity | high-pressure water supply quantity (l) Max. P Compressed quantity | quantity (l) by Max. 21 MPa low-pressure booster | quantity (l) by Max. 75 MPa high-pressure booster | Total water quantity (l) |
|---|---|---|---|---|---|
|  | 4.66 | 10.95 | 11.32 | 13.17 | 24.5 |
| 8" | 4.19 | 1.20 | 11.95 | 3.79 | 15.7 |
| 8" | 5.43 | 11.42 | 13.19 | 14.01 | 27.2 |
| 9⅝" | 5.22 | 0.64 | 14.88 | 3.86 | 18.7 |
| 9⅝" | 6.76 | 12.04 | 16.43 | 15.26 | 31.7 |
| 10¾" | 8.44 | 0.00 | 24.51 | 0.00 | 24.5 |
| 10¾" | 8.44 | 12.57 | 20.49 | 16.58 | 37.1 |
| 12" | 11.86 | 0.00 | 34.46 | 0.00 | 34.5 |
| 12" | 11.86 | 13.04 | 28.81 | 18.69 | 47.5 |
| 14" | 14.31 | 0.00 | 41.56 | 0.00 | 41.6 |
| 14" | 14.31 | 13.04 | 34.75 | 19.85 | 54.6 |
|  | 16.08 | 0.00 | 46.71 | 0.00 | 46.7 |
|  | 16.08 | 12.91 | 39.05 | 20.57 | 59.6 |
| 16" | 18.69 | 0.00 | 54.28 | 0.00 | 54.3 |
| 16" | 18.69 | 12.57 | 45.38 | 21.47 | 66.9 |
|  | 20.53 | 0.00 | 59.64 | 0.00 | 59.6 |
|  | 20.53 | 12.23 | 49.87 | 22.01 | 71.9 |
| 20" | 29.20 | 0.00 | 84.81 | 0.00 | 84.8 |
| 20" | 29.20 | 9.87 | 70.91 | 23.78 | 94.7 |
| 21" | 31.78 | 0.00 | 92.32 | 0.00 | 92.3 |
| 21" | 31.78 | 0.00 | 92.32 | 0.00 | 92.3 |

The following shows an example of a cycle time required for one test: 6.0 seconds for loading and unloading of a test pipe; 1.0 second for centering of the test pipe; 4.0 seconds for making a tail head advance; 6.0 to 9.5 seconds for supplying non-pressure water; 0.5 seconds for operation on an air extraction valve; 3.5 to 10 seconds for forcible supply of pressure water to achieve a test pressure; 10 seconds as a holding time; 0.5 seconds for depressing; 3.0 seconds for making the tail head retract; 1.0 second for ejecting the test pipe; and 1.5 to 3.0 seconds as a time lag. As a result, the cycle time fell within a range from 37.0 to 47.5 seconds. A time of this forcible supply of pressure water varied for reason of differing test pressures. A time of this forcible supply of pressure water is shorted significantly by the water hydraulic test method of this embodiment. The conventional water hydraulic test method inherently makes it impossible to conducting a test itself using one device on test pipes of such various types.

As long as two or more servo motor driven pumps 44 forming the principal part of the drive system 42 are prepared, the number of these pumps 44 is determined appropriately in a manner that depends on the performance of each pump 44 and characteristics required for each pump 44.

A test pipe having passed the aforementioned water hydraulic test is subjected to thread cutting at a pipe end for a connection to a pipe joint in a subsequent step. After a thread is cut in the test pipe, the test pipe is subjected to the same water hydraulic test with a pipe joint attached at one or each of opposite ends thereof. If the test pipe is subjected to the water hydraulic test with a pipe joint attached only to one end thereof, high-pressure water is supplied into a special plug including a plug for hermetically sealing the end of the test pipe and an integrated plug for hermetically sealing an open side of the pipe joint to check water leakage from a threaded part. Thus, this test is conducted using high-pressure water of a smaller quantity than a test conducted by filling the inside of the pipe entirely with water. However, this test is conducted at a high pressure like in Examples, so that pressure increase still takes time. Thus, the water hydraulic test method and the water hydraulic test device of Examples still work extremely effectively in a water hydraulic test on such a pipe end to achieve the effect of reducing a test time significantly.

In the description given above, an electric resistance welded pipe is shown as a test target. Meanwhile, this invention is also applicable to a water hydraulic test on a seamless pipe. The water hydraulic test on the seamless pipe involves a test pressure for example of 160 MPa higher than that of a test on an electric resistance welded pipe. Thus, it is desirable that three or more booster cylinders be used. Further, eight or nine servo motor driven pumps are required if the output of such a pump is 15 kW. The water hydraulic test on an electric resistance welded pipe may also be conducted using three or more booster cylinders.

REFERENCE SINGS LIST

10 Test pipe
20A Headstock unit
20B Tailstock
21 Air extraction valve
30 Low-pressure water supply system
31 Water tank
32 Pool
33 Water sump
34 Pump
35 On-off valve
40 High-pressure water supply system
41 Booster cylinder
42 Drive system for booster cylinder 41
43 Switching mechanism (solenoid valve)
44 Servo motor driven pump
45 Oil sump
47 Water hydraulic sensor
48 Control system

The invention claimed is:

1. A water hydraulic test method of conducting a water hydraulic test on a manufactured metal pipe by increasing a pressure in the metal pipe to a predetermined test pressure and holding the test pressure for a predetermined time by supplying high-pressure water from an oil hydraulically driven booster cylinder into the metal pipe, wherein
   a plurality of servo motor driven pumps connected in parallel is used as an oil hydraulic drive source for the booster cylinder,
   before a pressure on an output side of the booster cylinder reaches a switching point pressure set further lower by a predetermined pressure than the test pressure set in advance, the plurality of servo motor driven pumps operates simultaneously, and
   after the pressure on the output side of the booster cylinder reaches the switching point pressure, the plurality of servo motor driven pumps stops operating except one and the pressure on the output side of the booster cylinder is increased to the test pressure and the test pressure is held by operation of the one servo motor driven pump.

2. The water hydraulic test method according to claim 1, wherein the servo motor driven pumps are dual-displacement pumps.

3. The water hydraulic test method according to claim 1, wherein
   a water pressure P of high-pressure water is measured on the output side of the booster cylinder during pressure increase,
   the plurality of servo motor driven pumps operates simultaneously before the measured water pressure reaches the switching point pressure,
   when the measured water pressure reaches the switching point pressure, the plurality of servo motor driven pumps stops operating except one, and
   when the measured pressure reaches the test pressure, the one servo motor driven pump in operation is stopped.

4. The water hydraulic test method according to claim 1, wherein
   a plurality of booster cylinders is arranged in parallel with respect to the metal pipe, the booster cylinders having respective boosting ratios increasing in stages, and
   the booster cylinders are used in turn in order of increasing boosting ratio.

5. A water hydraulic test device of conducting a water hydraulic test on a manufactured metal pipe by increasing a pressure in the metal pipe to a predetermined test pressure and holding the test pressure for a predetermined time by supplying high-pressure water from an oil hydraulically driven booster cylinder into the metal pipe, wherein
   a plurality of servo motor driven pumps used as an oil hydraulic drive source for the booster cylinder is connected in parallel with respect to the booster cylinder,
   the booster cylinder includes a plurality of booster cylinders connected in parallel with respect to the metal pipe, the booster cylinders having respective boosting ratios increasing in stages, and a switching mechanism is provided between the oil hydraulic drive source and the plurality of booster cylinders, the switching mechanism supplying pressure oil from the oil hydraulic drive source selectively to one of the plurality of booster cylinders.

6. The water hydraulic test device according to claim 5, wherein the servo motor driven pumps are dual-displacement pumps.

7. The water hydraulic test device according to claim 5, wherein a water hydraulic sensor used for measuring the water pressure of high-pressure water is provided in a line on an output side of each of the booster cylinder, the water hydraulic test device comprising a cylinder control system configured to control the switching mechanism based on a water pressure measured using the water hydraulic sensor in such a manner that the booster cylinders operate in turn in order of increasing boosting ratio.

8. The water hydraulic test device according to claim 5, wherein a switching point pressure lower by a predetermined pressure than the test pressure is set, the water hydraulic test device comprising a pump control system configured to control the plurality of servo motor driven pumps in such a manner that the plurality of servo motor driven pumps operates simultaneously before a measured water pressure reaches the switching point pressure, and that one of the servo motor driven pumps operates thereafter before the measured pressure P reaches the test pressure.

* * * * *